(12) United States Patent
Tortelli et al.

(10) Patent No.: US 7,157,600 B2
(45) Date of Patent: Jan. 2, 2007

(54) PROCESS FOR PREPARING (PER) FLUOROHALOGENETHERS

(75) Inventors: Vito Tortelli, Milan (IT); Pierangelo Calini, Milan (IT); Stefano Millefanti, Como (IT)

(73) Assignee: Solvay Solexis S.p.A., Milan (IT)

( * ) Notice: Subject to any disclaimer, the term of this patent is extended or adjusted under 35 U.S.C. 154(b) by 307 days.

(21) Appl. No.: 10/795,995

(22) Filed: Mar. 10, 2004

(65) Prior Publication Data
US 2004/0199009 A1 Oct. 7, 2004

(30) Foreign Application Priority Data
Mar. 11, 2003 (IT) .................... MI2003A0444

(51) Int. Cl.
*C07C 39/82* (2006.01)
(52) U.S. Cl. .................... 562/825; 568/32; 568/35
(58) Field of Classification Search ............... 568/32, 568/35; 562/825
See application file for complete search history.

(56) References Cited

U.S. PATENT DOCUMENTS

| | | | |
|---|---|---|---|
| 3,282,875 A | 11/1966 | Connolly et al. | 524/795 |
| 4,358,412 A | 11/1982 | Ezzell et al. | 558/142 |
| 4,466,881 A | 8/1984 | Hamada et al. | 205/430 |
| 4,597,913 A | 7/1986 | Kimoto et al. | 558/436 |
| 4,801,409 A | 1/1989 | Marraccini et al. | 562/825 |
| 4,816,599 A | 3/1989 | Gregorio et al. | 560/300 |
| 4,827,024 A | 5/1989 | Guglielmo et al. | 560/300 |
| 4,962,282 A | 10/1990 | Marraccini et al. | 562/825 |
| 6,388,139 B1 | 5/2002 | Resnick | 568/32 |

FOREIGN PATENT DOCUMENTS

| | | |
|---|---|---|
| EP | 0 041 738 A1 | 12/1981 |
| EP | 0 201 871 A1 | 11/1986 |
| EP | 0 267 626 A1 | 5/1988 |
| EP | 1 388 531 A1 | 2/2004 |

OTHER PUBLICATIONS

Carl G. Krespan, Journal of Fluorine Chemistry, 16, "Fragmentation of Fluorosulfonyldiflyoroacetyl Fluoride Induced by Fluoride Ion," 1980, pp. 385-390.
I.L. Knunyants and G.A. Sokolski, Angew. Chem. Internat. Edit., vol. II "Fluorinated B-Sultones," 1972, pp. 583-595.
T. Gramstad and R.N. Haszeldine, J. Chem. Soc., "Perfluoroalkyl Derivatives of Sulphur," 1953, pp. 173-180.

*Primary Examiner*—Rosalynd Keys
(74) *Attorney, Agent, or Firm*—Arent Fox PLLC

(57) ABSTRACT

A process for preparing (per)fluorohalogenethers containing the —$SO_2F$ group, having general formula (I):

$$FSO_2-R-CF_2OCAF-CA'F_2 \qquad (I)$$

wherein:
  A and A', equal to or different from each other, are Cl or Br;
  R has the following meanings: a (per)fluorinated, preferably perfluorinated, substituent, optionally containing one or more oxygen atoms;
by reaction of carbonyl compounds having formula (II):

$$FSO_2-R-COF \qquad (II)$$

wherein R is as above;
in liquid phase with elemental fluorine and with olefinic compounds having formula (III):

$$CAF=CA'F \qquad (III)$$

wherein A and A' are as above,
operating at temperatures from −120° C. to −20° C., optionally in the presence of a solvent inert under the reaction conditions.

18 Claims, No Drawings

PROCESS FOR PREPARING (PER) FLUOROHALOGENETHERS

The present invention relates to a process for the preparation of fluorosulphonic group (—SO$_2$F) containing fluorinated vinylethers.

More specifically the present invention relates to the preparation of —SO$_2$F group containing fluorohalogenethers, which by dehalogenation give the corresponding fluorinated vinylethers, said process having improved selectivity combined with a lower formation of non recyclable by-products.

The fluorosulphonic vinylethers form a class of monomers useful for obtaining polymers containing —SO$_2$F groups, which are used in electrochemical applications as membranes for chloro-soda cells, fuel cells or as acid catalysts in organic synthesis.

Processes for obtaining fluorohalogenethers containing the —SO$_2$F group are known in the prior art.

U.S. Pat. No. 4,358,412 describes the synthesis of the fluorosulphonic vinylether CF$_2$=CF—O—CF$_2$CF$_2$SO$_2$F, wherein in the first step the compound FOC—CF(CF$_2$Cl)—O—(CF$_2$)$_2$SO$_2$F is obtained, by reacting the acylfluoride FOC—CF$_2$—SO$_2$F with the perfluoroallylchloride epoxide. In the second step the alkaline pyrolysis is carried out with sodium carbonate obtaining the fluorosulphonic vinylether. The fluorosulphonic vinylether synthesis according to this scheme has the drawback to use the perfluoroallylchloride epoxide which is a very expensive and not easily available reactant.

U.S. Pat. Nos. 4,962,282 and 4,801,409 describe the synthesis in gaseous phase of the hypofluorite FSO$_2$CF$_2$CF$_2$OF starting, respectively, from β sultone of tetrafluoroethylene having formula:

or from acylfluoride FSO$_2$CF$_2$COF.

The sulphonic hypofluorite can then be added up, according to the prior art, to 1,2-dichloro-1,2-difluoroethylene (CFC 1112). By dechlorination the monomer CF$_2$=CF—O—CF$_2$CF$_2$SO$_2$F is obtained. This process has the drawback to use the sulphonic hypofluorite, a strongly oxidizing compound requiring, as well known, particular precautions in the use. Besides, the Applicant has found that in the reaction with the olefin the yields are not satisfactory owing to the hypofluorite decomposition (see the comparative Example).

Generally the drawback of said processes is to have to synthesize the hypofluorite which, as known, is an unstable compound, and, therefore, must be immediately used. Furthermore the synthesis of this compound requires the use of a catalyst and therefore from the industrial point of view the process implies additional costs for the catalytic section management and the catalyst regeneration.

Generally, for the hypofluorite preparation the most known processes use catalysts based on metal fluorides.

In U.S. Pat. No. 4,827,024 it is described the preparation in a continuous way of hypofluorites, by the fluorination reaction in equimolecular amounts with fluorine and halogenated carbonyl compounds having at least two carbon atoms, in the presence of a catalyst formed of CsF, optionally in admixture with metals, for example copper. Generally said metals are used, besides as catalyst (CsF) supports, also to make easier the thermal exchange and to dissipate the heat generated in the hypofluorite synthesis. The metal support according to the above described prior art must satisfy two main functions: 1) to maintain the catalyst in a form accessible to reactants, 2) to make the thermal exchange easier maintaining controllable, in the required range, the catalytic bed temperature.

The drawback of this process is to use hypofluorites and a catalyst, with the above drawbacks.

In U.S. Pat. No. 4,816,599, U.S. Pat. No. 4,801,409 and U.S. Pat. No. 4,962,282 hypofluorites are prefarably prepared by reaction of the acylfluoride with excess of fluorine to have complete conversion to hypofluorite, so to reduce as much as possible the acylfluoride concentration on the catalytic bed and avoid possible decomposition reactions of acylfluorides in the presence of CsF. See for example Carl G. Krespan in Journal of Fluorine Chemistry, 16 (1980) 385–390.

A further drawback of said processes concerns the catalyst poisoning. Tests carried out by the Applicant on the processes for the preparation of hypofluorites of the prior art wherein the above described catalysts are used, have shown that by using said catalytic systems, both in a discontinuous and continuous way, their activity rapidly decreases in the time. The Applicant has found in particular that the activity reduction is very marked, until the complete catalyst deactivation, when in the hypofluorite formation reaction an excess of fluorine on the stoichiometric value is used, condition indicated as preferred in the mentioned processes of the prior art.

The need was therefore felt to have available a process for the preparation of —SO$_2$F containing fluorohalogenethers overcoming the drawbacks of the prior art, in particular avoiding the use of catalysts and the hypofluorite synthesis, improving the selectivity in the desired compounds and with a lower formation of non recyclable by-products.

The Applicant has surprisingly and unexpectedly found that by using the process described hereinafter it is possible to solve said technical problem.

An object of the present invention is a process for preparing (per)fluorohalogenethers containing the —SO$_2$F group and having general formula (I):

FSO$_2$—R—CF$_2$OCAF—CA'F$_2$ (I)

wherein:

A and A', equal to or different from each other, are Cl or Br;

R can have the following meanings: a (per)fluorinated, preferably perfluorinated, substituent selected from the following groups: linear or branched C$_1$–C$_{20}$ alkyl, C$_3$–C$_7$ cycloalkyl; aromatic, C$_6$–C$_{10}$ arylalkyl or alkylaryl; C$_5$–C$_{10}$ heterocyclic or alkylheterocyclic; optionally containing one or more oxygen atoms;

when R is fluorinated it can optionally contain one or more H atoms and/or one or more halogen atoms different from F;

by reacting carbonyl compounds having formula (II):

FSO$_2$—R—COF (II)

wherein R is as above;

in liquid phase with elemental fluorine and with olefinic compounds having formula (III):

CAF=CA'F (III)

wherein A and A' are as above, operating at temperatures from −120° C. to −20° C., preferably from −100° C. to −40° C., optionally in the presence of a solvent inert under the reaction conditions.

The fluorine used in the reaction can optionally be diluted with an inert gas such for example nitrogen or helium.

The carbonyl compounds of formula (II) can be synthesized with known methods of the prior art. For example the compounds $FSO_2CF_2COF$ and $FSO_2CF(CF_3)COF$ can be prepared according to the method described in Angew. Chem. Internat. Edit./vol.11 (1972) No. 7 page 583. The compounds $FSO_2CF_2CF_2OCF(CF_3)COF$ and $FSO_2CF_2CF_2OCF(CF_3)CF_2OCF(CF_3)COF$ can be prepared according to the method described in U.S. Pat. No. 3,282,875.

$FSO_2(CF_2)_3OCF(CF_3)COF$ can for example be prepared according to U.S. Pat. No. 4,597,913 by reacting $FSO_2CF_2CF_2COF$, obtained for example according to U.S. Pat. No. 4,466,881, and HFPO (hexafluoropropene epoxide).

The formula (III) compounds usable in the present invention process are for example 1,2-dichloro-1,2-difluoroethylene (CFC 1112), 1,2-dibromo-1,2-difluoroethylene, preferably CFC 1112 is used.

As solvents in the present invention process, compounds, liquid and inert in the above mentioned temperature range can be used. Compounds selected from (per)-fluorocarbons, (per)fluoroethers, (per)fluoropolyethers, perfluoroamines, or their mixtures, can for example be used. Solvents can also be used having a low GWP, for example fluoropolyethers containing at least one hydrogen atom in one end group, preferably in both end groups; fluoroethers containing non fluorinated end groups of the type $OR_a$ wherein $R_a$ is an alkyl from 1 to 3 carbon atoms, for example $OCH_3$, $OC_2H_5$, $OC_3F_7$ the other end group can be the same or a perfluorinated group, a hydrogen fluoro containing group. The skilled man in the art is able to select in the above classes the compounds to be used as solvents on the basis of their physical properties, for example to be easily separable from the components of the reaction mixture.

As said, when R is fluorinated, it can optionally contain one or more H atoms and/or one or more halogen atoms different from F. The halogen atoms are Cl, Br, I, preferably Cl.

The process according to the present invention can be carried out in a semicontinuous or a continuous way. Preferably it is carried out in a sole reactor.

The semicontinuous process can for example be carried out by feeding gaseous fluorine into the reactor containing the formula (II) acyl fluorides and the formula (III) olefins. The reaction is exothermic. The molar ratio (II):(III) can vary in a wide range, for example between 10:1 and 1:20. The fluorine feeding in the semicontinuous process can be continued up to the total olefin conversion. This is easily determined since the reaction exothermy is no longer noticed. The used amount by moles of fluorine is generally equal to the amount by moles of (III), generally lower. Preferably one operates with molar amounts equal to (III) to have the total conversion of (III).

In the continuous process the gaseous fluorine and compounds (II) and (III) are fed into the reactor, until reaching the steady state. In practice the reactants are fed into the reactor with established flow-rates and the reaction mixture is continuously drawn. The steady state is reached when the concentration of the three reactants and of the reaction compounds in the reactor is equal to the concentration of the reactants and reaction compounds outflowing from the reactor. The molar ratios among the reactants are not particularly binding for the present invention process, for example the molar ratio (II):(III) is as defined for the semicontinuous process, the molar ratio $F_2$:(III) ranges from 1:20 to 10:1.

The Applicant has surprisingly and unexpectedly found that the reaction among a compound (II), the formula (III) olefin and elemental fluorine, in the temperature range of the invention process, directly supplies formula (I) fluorohalogenethers with improved selectivity in comparison with the processes of the prior art (see the comparative Examples) Besides, with the invention process one can operate at partial conversion of compound (II), thus recycling the unreacted compound (II). This is not possible with the process indicated in the comparative Example. The invention process results are therefore quite surprising and unexpected with respect to the teachings of the prior art. Furthermore in the invention process there is a further advantage since no catalyst is used, as on the contrary indicated in the prior art for obtaining fluorohalogenethers from the precursor hypofluorite. The catalyst absence notably simplifies the process for obtaining fluorohalogenethers, particularly on an industrial scale since the plant section with the catalytic reactor, the preparation and regeneration of the catalyst are eliminated.

Therefore with the invention process there is a higher productivity since there are no plant stops for the catalyst regeneration or substitution.

The Applicant has furthermore found that in the reaction mixture obtained with the process according to the present invention, the decomposition products deriving from compound (II) are present in reduced amounts (see the Examples).

It has been found that with the present invention process it is suitable to operate at partial conversion of compound (II), for example conversions from 10% to 40% preferably from 10% to 20%, to obtain improved selectivity in the fluorohalogenether and have a high amount of recyclable fraction. Indeed the unreacted formula (II) compounds, differently from hypofluorites (see the comparative Example 1), do not decompose in the reaction environment and can be recovered, for example by distillation, and used again. In the processes for obtaining fluorohalogenethers of the prior art wherein hypofluorites are used, it is not possible to separate and recycle hypofluorites, due to the dangerousness and unstableness of said compounds. It is well known that when hypofluorites are used, they are let completely react without accumulation in the reaction environment.

The (per)fluorohalogenethers containing the —$SO_2F$ group and having general formula (I) can be transformed into (per)fluorohalogenoethers containing the —$SO_3H$ group by hydrolysis of the sulphonyl fluorides according to known processes, for example as described by T. Gramstad et al., J. Chem. Soc. 1956, 173, in aqueous alkaline solutions, for example aqueous solutions of KOH, NaOH, $NH_4OH$. From said solutions the sulphonic salt is recovered as a solid. By means of a strong acid, such for example sulphuric acid, the salt is then converted into the corresponding acid, which can be recovered for example by distillation.

The same activation can be carried out on vinylethers obtained by dehalogenation of the formula (I) fluorohalogenethers containing the —$SO_2F$ group.

The dehalogenation of the formula (I) fluorohalogenethers can be carried out by using the method described in U.S. Pat. No. 6,388,139.

The following Examples illustrate with non limitative purposes the invention.

EXAMPLES

Example 1 Comparative

Synthesis of $FSO_2-CF_2-CF_2O-CFCl-CF_2Cl$ According to the Prior Art 1.5 Nl/h of fluorine diluted with nitrogen (molar ratio fluorine/nitrogen 1/14) and 1.1 Nl/h of $SO_2F-CF_2-COF$ are fed into a 500 cc metal reactor filled with CsF as catalyst mixed with copper wires to disperse the reaction heat. The acylfluoride is converted with a yield of 99.5% into hypofluorite $SO_2F-CF_2-CF_2OF$. The so produced hypofluorite is further diluted with nitrogen (molar ratio hypofluorite/nitrogen 1/35) and fed into a CSTR type reactor (continous stirred tank reactor) containing 69 g of $CFCl=CFCl$ (CFC 1112) and 453 g of $CF_2Cl-CF_3$ (CFC 115) as reaction solvent and maintaind at the temperature of −85° C.

After 4 hours the reactor is discharged and the solution is analyzed by gaschromatography.

The reaction mass balance is 97.1%. The hypofluorite conversion is 100% and its selectivity in $FSO_2-CF_2-CF_2O-CFCl-CF_2Cl$ (fluorosulphonic adduct) is 41.5%. Decomposition by-products of the hypofluorite (total selectivity referred to the acylfluoride 39.5%) and other by-products (selectivity referred to the acylfluoride 19%) are also present.

The solution is distilled obtaining 27 g of fluorosulphonic adduct pure at 98.5% (yield: 38.8%).

Example 2

Synthesis of $FSO_2-CF_2-CF_2O-CFCl-CF_2Cl$ 441 g of $CF_2Cl-CF_3$ (CFC 115) are introduced into the CSTR reactor of the Example 1, maintained at the temperature of −80° C. Then 3.9 Nl/h of fluorine diluted with nitrogen (molar ratio fluorine/nitrogen 1/5), 3.1 Nl/h of $CFCl=CFCl$ (CFC 1112) and 3.9 Nl/h of $SO_2F-CF_2-COF$ are fed.

The reaction is carried out for 3 hours, then the reactor is discharged: the material balance is 97.4%. The reaction raw product is distilled in metal column and the obtained fractions analyzed by gaschromatography and $^{19}F$ NMR. The CFC 1112 conversion is complete and that of the acylfluoride is 57.8%.

52.7 g of fluorosulphonic adduct $FSO_2-CF_2-CF_2O-CFCl-CF_2Cl$ are separated. The selectivity is 49.8%.

39.6 g of acylfluoride are recovered.

Parallelly to the main reaction it also takes place the fluorination reaction of CFC 1112 to CFC 114 and of fluorodimerization to $CF_2Cl-CFCl-CFCl-CF2Cl$ (CFC 1112 dimer). The selectivity with respect to CFC 1112 is 57.7% for CFC 114 and 0.5% for CFC 1112 dimer.

The CFC 1112 molar balance is 99%.

Example 3

Synthesis of $FSO_2-CF_2-CF_2O-CFCl-CF_2Cl$ in Excess of Acylfluoride

The Example 2 is repeated under the same conditions introducing into the CSTR reactor 128.9 g of $SO_2F-CF_2-COF$ together with 311.1 g of solvent (CFC 115) and feeding 3.9 Nl/h of fluorine diluted with nitrogen (molar ratio fluorine/nitrogen 1/5), 3.1 Nl/h of $CFCl=CFCl$ (CFC 1112) and 3.9 Nl/h of $SO_2F-CF_2-COF$ for 3 hours.

The reaction mass balance is 97.6%.

Analogously to the Example 2 the reaction raw product is distilled in metal column and the obtained fractions are analyzed by gaschromatography and $^{19}F$ NMR. The CFC 1112 conversion is complete and that of the fed acylfluoride is 29%.

34.2 g of fluorosulphonic adduct $FSO_2-CF_2-CF_2O-CFCl-CF_2Cl$ are separated. The selectivity is 65.0%.

195.9 g of acylfluoride are recovered.

Beside the main reaction there is also the reaction of fluorination of CFC 1112 to CFC 114 and of fluorodimerization to $CF_2Cl-CFCl-CFCl-CF2Cl$ (CFC 1112 dimer). The selectivity with respect to CFC 1112 is 44.9% for CFC 114 and 0.34% for CFC 1112 dimer.

The molar balance of CFC 1112 is 99%.

The invention claimed is:

1. A process for preparing (per)fluorohalogenethers containing the $-SO_2F$ group and having general formula (I):

$$FSO_2-R-CF_2OCAF-CA'F_2 \qquad (I)$$

wherein:
A and A', equal to or different from each other, are Cl or Br;
R has the following meanings: a (per)fluorinated substituent, selected from the following groups: linear or branched $C_1-C_{20}$ alkyl, $C_3-C_7$ cycloalkyl; aromatic, $C_7-C_{10}$ arylalkyl or alkylaryl; $C_5-C_{10}$ heterocyclic or alkylhetero-cyclic;
optionally containing one or more oxygen atoms;
when R is fluorinated, it can optionally contain one or more H atoms and/or one or more halogen atoms different from F;
by reaction of carbonyl compounds having formula (II):

$$FSO_2-R-COF \qquad (II)$$

wherein R is as above;
in liquid phase with elemental fluorine and with olefinic compounds having formula (III):

$$CAF=CA'F \qquad (III)$$

wherein A and A' are as above,
by operating at temperatures from −120° C. to −20° C., optionally in the presence of a solvent inert under the reaction conditions.

2. A process according to claim 1, wherein the fluorine is diluted with an inert gas selected between nitrogen or helium.

3. A process according to claim 1, wherein the formula (III) compounds are selected from 1,2-dichloro-1,2-difluoroethylene (CFC 1112) and 1,2-dibromo-1,2-difluoroethylene.

4. A process according to claim 1, wherein the solvent is selected from the group consisting of the following compounds: (per)fluorocarbons, (per)fluoroethers, (per)fluoropolyethers, perfluoroamines, or respective mixtures; fluoropolyethers containing at least one hydrogen atom in one end group, fluoroethers containing at least one hydrogen atom in one end group, or containing non fluorinated end groups of the type $OR_a$ wherein $R_a$ is an alkyl from 1 to 3 carbon atoms.

5. A process according to claim 1, wherein, when R in formula (I) is fluorinated, it optionally contains one or more H atoms and/or one or more halogen atoms different from F.

6. A process according to claim 1 carried out in a semicontinuous or a continuous way.

7. A semicontinuous process according to claim 6, wherein the molar ratio (II):(III) ranges from 10:1 to 1:20 and the used amount by moles of fluorine is equal to or lower than the amount by moles of (III).

8. A continuous process according to claim 6, wherein the molar ratio (II):(III) is as defined in claim 7 and the molar ratio $F_2$:(III) ranges from 1:20 to 10:1.

9. A process according to claim 1, wherein one operates at partial conversion of compound (II).

10. A process for preparing (per)fluorohalogenethers containing the —$SO_2F$ group and having general formula (I):

$$FSO_2—R—CF_2OCAF—CA'F_2 \quad (I)$$

wherein:

A and A', equal to or different from each other, are Cl or Br:

R can have the following meanings: a (per)fluorinated substituent, selected from the following groups: linear or branched $C_1$–$C_{20}$ alkyl, $C_3$–$C_7$ cycloalkyl; aromatic, $C_6$–$C_{10}$ arylalkyl or alkylaryl; $C_5$–$C_{10}$ heterocyclic or alkylheterocyclic;

optionally containing one or more oxygen atoms;

when R is fluorinated, it can optionally contain one or more H atoms and/or one or more halogen atoms different from F;

by reaction of carbonyl compounds having formula (II):

$$FSO—R—COF \quad (II)$$

wherein R is as above:

in liquid phase with elemental fluorine and with olefinic compounds having formula (III):

$$CAF═CAF \quad (III)$$

wherein A and A' are as above, by operating at temperatures from −120° C. to −20° C., optionally in the presence of a solvent inert under the reaction conditions, and wherein a dehalogenation step is carried out to obtain fluorinated vinylethers.

11. A process accordingly to claim 1, wherein R is a perfluorinated substituent.

12. A process accordingly to claim 1, wherein the temperatures are from −100° C. to −40° C.

13. A process according to claim 3, wherein the formula (III) compounds are CFC 1112.

14. A process according to claim 4, wherein the fluoropolyethers contain at least one hydrogen atom in both end groups.

15. A process according to claim 4, wherein the fluoroethers contain at least one hydrogen atom in both end groups.

16. A process according to claim 5, wherein the one or more halogen atoms is Cl.

17. A process according to claim 9, wherein the conversion ranges are from 10% to 40%.

18. A process according to claim 17, wherein the conversion ranges are from 10% to 20%.

* * * * *